(12) United States Patent
Carriazo

(10) Patent No.: US 6,656,196 B1
(45) Date of Patent: Dec. 2, 2003

(54) MICROKERATOME CUTTING BLADE AND METHOD FOR PERFORMING CORNEAL RESECTIONS

(76) Inventor: Cesar C. Carriazo, KRA 53 #82-202 Apto 5B, Barranquilla (CO)

( * ) Notice: Subject to any disclaimer, the term of this patent is extended or adjusted under 35 U.S.C. 154(b) by 0 days.

(21) Appl. No.: 09/517,025

(22) Filed: Mar. 2, 2000

Related U.S. Application Data

(63) Continuation-in-part of application No. 09/375,154, filed on Aug. 16, 1999, now Pat. No. 6,296,650.
(60) Provisional application No. 60/128,851, filed on Apr. 12, 1999.

(51) Int. Cl.$^7$ .................................................. A61F 9/00
(52) U.S. Cl. ....................................... 606/166; 606/161
(58) Field of Search ............................... 606/166, 170, 606/167, 161; 604/22; 30/356, 357, 346.5, 346.55

(56) References Cited

U.S. PATENT DOCUMENTS

| | | | |
|---|---|---|---|
| 4,662,370 A | | 5/1987 | Hoffmanns et al. |
| 5,133,726 A | | 7/1992 | Ruiz et al. |
| 5,496,339 A | | 3/1996 | Koepnick |
| 5,586,980 A | | 12/1996 | Kremer et al. |
| RE35,421 E | | 1/1997 | Ruiz et al. |
| 5,624,456 A | | 4/1997 | Hellenkamp |
| 5,980,543 A | | 11/1999 | Carriazo et al. |
| 6,007,553 A | * | 12/1999 | Hellenkamp et al. ........ 606/166 |
| 6,051,009 A | * | 4/2000 | Hellenkamp et al. ........ 606/169 |
| 6,071,293 A | * | 6/2000 | Krumeich ................... 606/169 |
| 6,099,541 A | * | 8/2000 | Klopotek .................... 606/169 |
| 6,143,010 A | | 11/2000 | Slivestrini et al. |

FOREIGN PATENT DOCUMENTS

JP 0432325 A1 6/1991

OTHER PUBLICATIONS

Ministêere De L'Industrie; Brevet D'Invention: P.V N° 943.340 N° 1.366.323; Trêpan notamment pour chirurgie oculair; M. Heri Marie Louis Garrigue résidant en France (Seine); Dec. 28, 1964.

* cited by examiner

Primary Examiner—Corrine McDermott
Assistant Examiner—Thomas Barrett
(74) Attorney, Agent, or Firm—Streets & Steele; Jeffrey L. Streets; Steven L. Christian

(57) ABSTRACT

An improved microkeratome includes a guide ring assembly for placement on the ocular globe and means for temporarily fixing the guide ring to the ocular globe. A cutting head contains an improved cutting blade having an arcuate cutting edge suitable for corneal resections. A vertical support assembly is connected to the guide ring and supports the cutting head for rotation about a horizontal axis such that rotation of the cutting head about the horizontal axis moves the cutting blade along an arcuate cutting path into engagement with the cornea of the ocular globe, whereby the arcuate cutting edge of the cutting blade cuts a substantially rounded corneal disk. An improved method related to the use of the arcuate cutting blade is also provided.

7 Claims, 19 Drawing Sheets

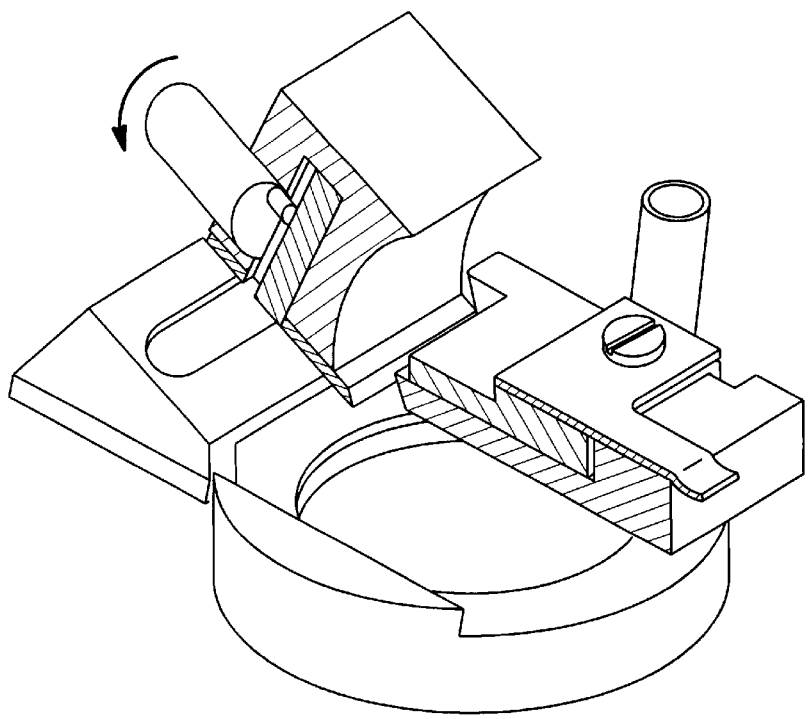
FIG. P1
(PRIOR ART)
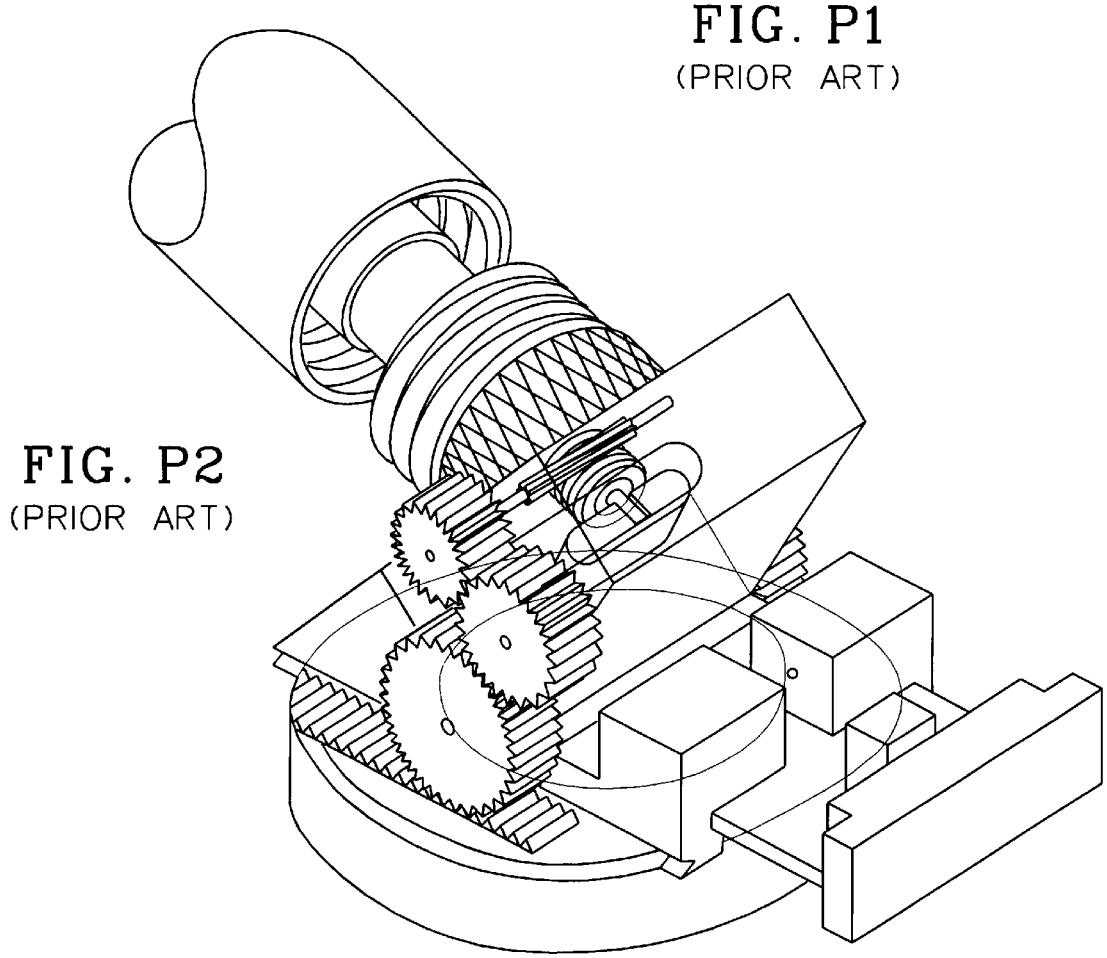
FIG. P2
(PRIOR ART)

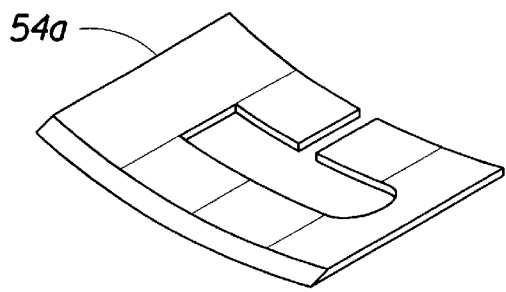
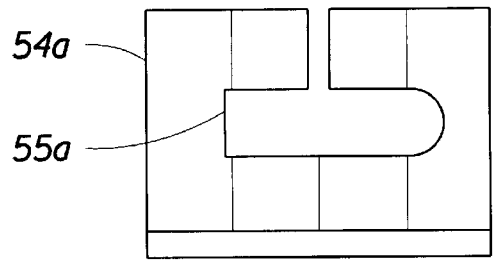
FIG. 12A          FIG. 12B
FIG. 12C
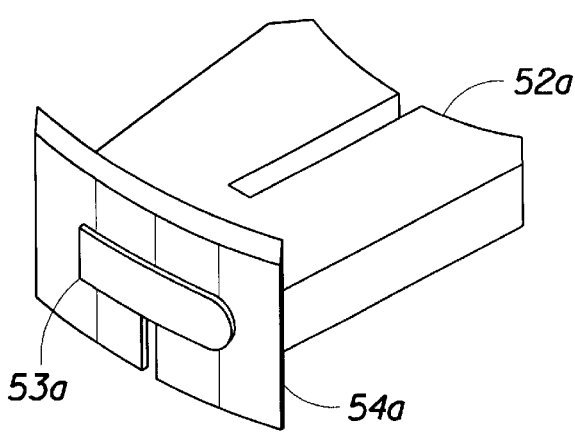
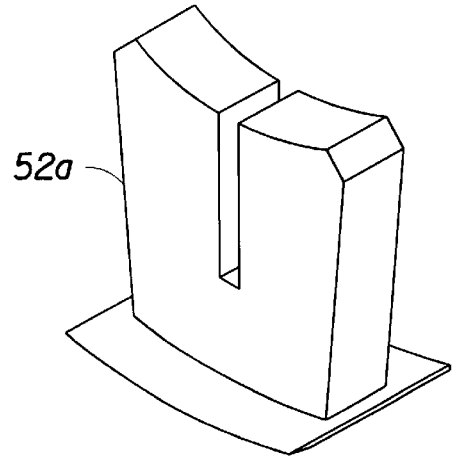
FIG. 13A          FIG. 13B

MICROKERATOME CUTTING BLADE AND METHOD FOR PERFORMING CORNEAL RESECTIONS

CROSS-REFERENCE TO RELATED APPLICATIONS

This application is a continuation-in-part of U.S. patent application Ser. No. 09/375,154 filed on Aug. 16, 1999, now U.S. Pat. No. 6,296,650, which claims priority to U.S. Provisional Application No. 60/128,851, filed on Apr. 12, 1999.

BACKGROUND OF THE INVENTION

1. Field of the Invention

The present invention relates to medical instruments and methods for performing eye surgery to correct irregularities of the cornea. More particularly, the present invention relates to mechanical instruments known as microkeratomes and the cutting blades utilized thereby, as well as related surgical methods for performing lamellar keratotomies.

2. The Related Art

The first microkeratome for performing corneal resections was developed in 1962 by the Doctor Jose I. Barraquer, and is shown generally in FIG. P1. This microkeratome includes a guide ring which is fixed to an ocular globe, or eyeball, with the aid of a partial vacuum applied through the guide ring. The guide ring immobilizes the ocular globe, maintains the tension of the globe, and aids in regulating the diameter of the corneal resection. A portion of the microkeratome called a cutting head is supported within a channel in the guide ring for guided linear movement of the microkeratome across the ring by the surgeon. The cutting head carries a cutting blade that is oscillated by a motor-driven eccentric transverse the channel as the instrument is moved through the cutting path defined by the channel. The cutting head carries a removable, lower planar member that compresses the ocular globe ahead of the oscillating blade, to permit the blade to cut a lamella having a lower surface that is parallel to the surface of the cornea that is compressed by the planar member. The planar member is interchangeable with similar planar members of differing thicknesses, so as to vary the thickness of the resectioned corneal "disk."

Numerous variations on the Barraquer microkeratome have been made since 1962, including the apparatus that is the subject of U.S. Pat. No. 4,662,370 assigned to Carl-Zeiss-Stiftung of Germany. The '370 patent describes a microkeratome having interchangeable inserts with convex, concave, and planar surfaces that engage and compress the cornea for producing a corneal resection of predetermined form and curvature. The inserts are set within a stationary planar member that is fixed to the guide ring. The cutting blade is moved through a cutting path parallel to the planar member defined by a gap between the planar member and the guide ring, and oscillates transverse the path.

While apparently effective to permit resections of corneal lenticula, the apparatus of the '370 patent lacks means for controlling, or automating the rate of movement by the cutting head across the guide ring, and is therefore prone to binding up in the corneal tissue, or otherwise producing imprecise resections under unsteady progress by the surgeon's hand. Furthermore, there is no apparent means for changing the depth or thickness of the corneal resection. Also, this apparatus is limited to use in lamellar keratectomies (excision of a corneal section), as opposed to lamellar keratotomies (incision through the cornea).

The problem of controlled movement across the guide ring has been addressed by the instrument described in U.S. Pat. No. 5,133,726, which has been reissued as Re 35,421, to Luis A. Ruiz and Sergio Lenchig G. The '726 and '421 patents disclose a microkeratome, shown in FIG. P2, having a gear transmission assembly for moving the instrument through the cutting path at a controlled rate of speed. The gears are driven by the same motor that drives the cutting blade and engage a track atop the guide ring. Thus, the automated transmission system is an improvement over the instrument of the '370 patent, but in practice it has been found that the weight of the motor in the instrument produces a large moment through the handle of the device. This moment, coupled with the forward positioning of the gear that engages the guide ring track, causes the rear surface of the cutting head to bind in its engagement with the guide ring. At best, this results in uneven travel by the instrument during the surgery and unnecessary pressure fluctuations within the eye. At worst, such binding can cause irregular cutting of the cornea that produces leucoma, or the induction of an astigmatism.

The relatively recent technological development of intrastromal refractive surgery led to the creation of instruments and methods for performing incomplete lamellar temporo-nasal keratotomies, which leave a peripheral residue of corneal tissue uncut to act as a "nasal hinge." The nasal hinge permits the corneal disk to be lifted for exposure and carving of the stromal layer, such as by a laser. The use of a laser to perform stromal carving in association with an incomplete lamellar keratotomy is referred to as "Laser Intrastromal Keratomileusis" ("LASIK").

In similar fashion to the original Barraquer device, the microkeratome of the '726 and '421 patents include a forward planar member in the lower portion of the cutting head that is interchangeable with similar planar members of varying thicknesses. For the planar member to be interchangeable, however, a slotted portion of the cutting head extends substantially forward of the cutting blade to receive the planar member. This, and the fact that the transmission gears are positioned outside the cutting head, result in a fairly large surface area, or "footprint" for the instrument. The large footprint restricts the manner in which the microkeratome can be used, and generally requires that it be moved across the cornea from the temporal region adjacent the eye, producing the vertical nasal hinge when performing incomplete lamellar keratotomies. The vertical nasal hinge has at least two deficiencies. First, the corneal disk resulting from the LASIK, or other procedure, will be vertically displaced after surgery, and/or pleated to some extent by the opening and closing of the upper eyelid. Second, the formation of a vertical nasal hinge on the corneal disk increases the likelihood of accidental ablation of the hinge during the correction of an astigmatism, which is typically performed with vertical cutting motions across a major diameter of the cornea.

The large surface area of the planar member, or plaque, described in the '726 patent is designed to substantially compress the entire cornea at any one time. Such action produces unnecessarily high intraocular pressure, which unduly stresses the eye and could result in complications during surgery.

Further problems with known microkeratomes have been observed in performing resections on patient's having small eyes. The smaller ocular structure, particularly the peripheral structure, of such patients presents great difficulty during a lamellar keratotomy, since a portion of the surgical instrument may collide with the ocular structure and cause surgical accidents. This problem persists because, in spite of all efforts to perform lamellar keratotomy with more reliable instruments, the physical size of the instruments and the required surface area that the instrument must occupy during a lemellar keratotomy increase the likelihood that some portion of the microkeratome structure will encounter the patient's ocular structure.

Another problem with known systems, such as the microkeratome described in U.S. Pat. No. 5,624,456, relates to the manner in which the cutting head is brought into contact with the corneal surface. More specifically, the microkeratome of the '456 patent induces movement of a cutting blade through a flat plane which is defined, by necessity, to clear the patient's ocular structure. For purposes of discussion, this plane may be considered to be a horizontal plane since the patient's head will be more or less horizontal during the procedure. In order for the cutting blade to intersect the cornea, the eye must be pulled outwardly over the ocular structures so as to place a portion of the cornea above the horizontal plane. This creates a risk of suction loss between the surgical guide ring and the eye during the operation, with potentially severe consequences.

Other problems in the related microkeratome art include the requirement of interacting drive gears which must be constantly maintained for smooth operation, and the limited options for placement of the suction orifice on the surgical guide ring. The latter problem is a result of the need to leave open a clear path or guideway in the guide ring for passage of the cutting head and cutting blade, since the cutting blade is carried in a flat, horizontal plane as described above.

It is an object of the present invention to address one or more of the shortcomings described herein, as well as others.

SUMMARY OF THE INVENTION

The objects and advantages of the present invention are achieved by an improved microkeratome and method for performing a lamellar keratotomy of an ocular globe. The microkeratome includes a guide ring assembly for placement on the ocular globe and means for temporarily fixing the guide ring to the ocular globe. A cutting head contains a cutting blade having an arcuate cutting edge suitable for corneal resections. A vertical support assembly is connected to the guide ring and supports the cutting head for rotation about a horizontal axis such that rotation of the cutting head about the horizontal axis moves the cutting blade along an arcuate cutting path into engagement with the cornea of the ocular globe, whereby the arcuate cutting edge of the cutting blade cuts a substantially rounded corneal disk.

The cutting blade may include a substantially rectangular plate having one of its edges sharpened for cutting. In a preferred embodiment, the plate has a smooth, continuous bend therein making the cutting edge arcuately shaped. The cutting blade preferably includes steel, and may comprise a stainless steel alloy. An opening is provided in the plate of the cutting blade for engagement by a blade-holding member of the microkeratome.

In a preferred embodiment, the microkeratome also includes means for rotating the cutting head about the horizontal axis to move the cutting blade at least partially through the cornea to create a corneal flap during a lamellar keratotomy. For this purpose, the cutting head includes an opening providing access to the support shaft. The rotating means include a housing adapted for connection to the cutting head at the opening therein. An output shaft is rotatably carried within the housing and has an outer portion extending from the housing for passage through the opening in the cutting head and engagement with the support shaft when the housing is connected to the cutting head. Means are carried within the housing for applying a torque to the output shaft, whereby the application of torque from the torque applying means to the output shaft induces rotation of the cutting head and the housing about the support shaft at a controlled speed.

It is further preferred that the cutting head include a support shaft extending laterally therethrough equipped with lateral support members on either end of the support shaft that extend from opposing sides of said cutting head for engagement with the vertical support assembly. Still further, it is preferred that the cutting head include means for oscillating the cutting blade back and forth through an arcuate path transverse the cutting head to facilitate a smooth incision by the cutting blade.

The vertical support assembly preferably includes a pair of members extending upwardly from the guide ring 180° apart from each other. Alternatively, the vertical support assembly includes a pair of opposing members separated 180° apart from each other in respect to the guide ring by a lateral support arm, the lateral support arm being supported above the guide ring by a vertical support arm extending upwardly from the guide ring.

The present invention further provides a method of performing corneal resections for a lamellar keratotomy, including the step of supporting a cutting head carrying a cutting blade having an arcuate cutting edge for rotation about a horizontal axis elevated above the patient's eye, and inducing rotation of the cutting head about the horizontal axis to move the cutting blade through a pendular cutting path that intersects the cornea.

Preferably, the cutting head is supported by fixing a guide ring to an ocular globe about the globe's cornea so that the cornea extends through and above the guide ring. The guide ring includes a support system extending upwardly therefrom, and the cutting head includes a support shaft adapted for alignment with the horizontal axis and constrained against rotation about the horizontal axis by the support system when the support shaft is placed in engagement with the support system. Rotation of the cutting head is induced by operating a motor to apply a torque to the constrained support shaft to drive the cutting head and move the cutting blade through a pendular cutting path that intersects the cornea. The movement of the cutting blade is stopped at a predetermined point along the cutting path whereby a hinged corneal cap is formed.

In another aspect, the present invention provides a method defined by the steps of fixing a guide ring to an ocular globe about the globe's cornea so that at least a portion of the cornea extends through and above the guide ring, and inducing rotation of a cutting head carrying a cutting blade about a horizontal axis elevated above the guide ring, whereby rotation of the cutting head moves the cutting blade through a pendular cutting path that intersects the portion of the cornea extending above the guide ring.

The cutting blade may have either an arcuate cutting edge whereby the rotation of the cutting head produces a substantially round-shaped corneal disk, or a straight cutting edge whereby the rotation of the cutting head produces a substantially oval-shaped corneal disk. Alternatively, the arcuate cutting edge may be shaped so as to produce a substantially oval-shaped corneal disk, as appropriate for the desired correction.

BRIEF DESCRIPTION OF THE DRAWINGS

In the drawings, wherein like reference characters are used throughout to describe like parts:

FIG. P1 is a perspective view, partially in section, of the original Barraquer microkeratome;

Figure 1:
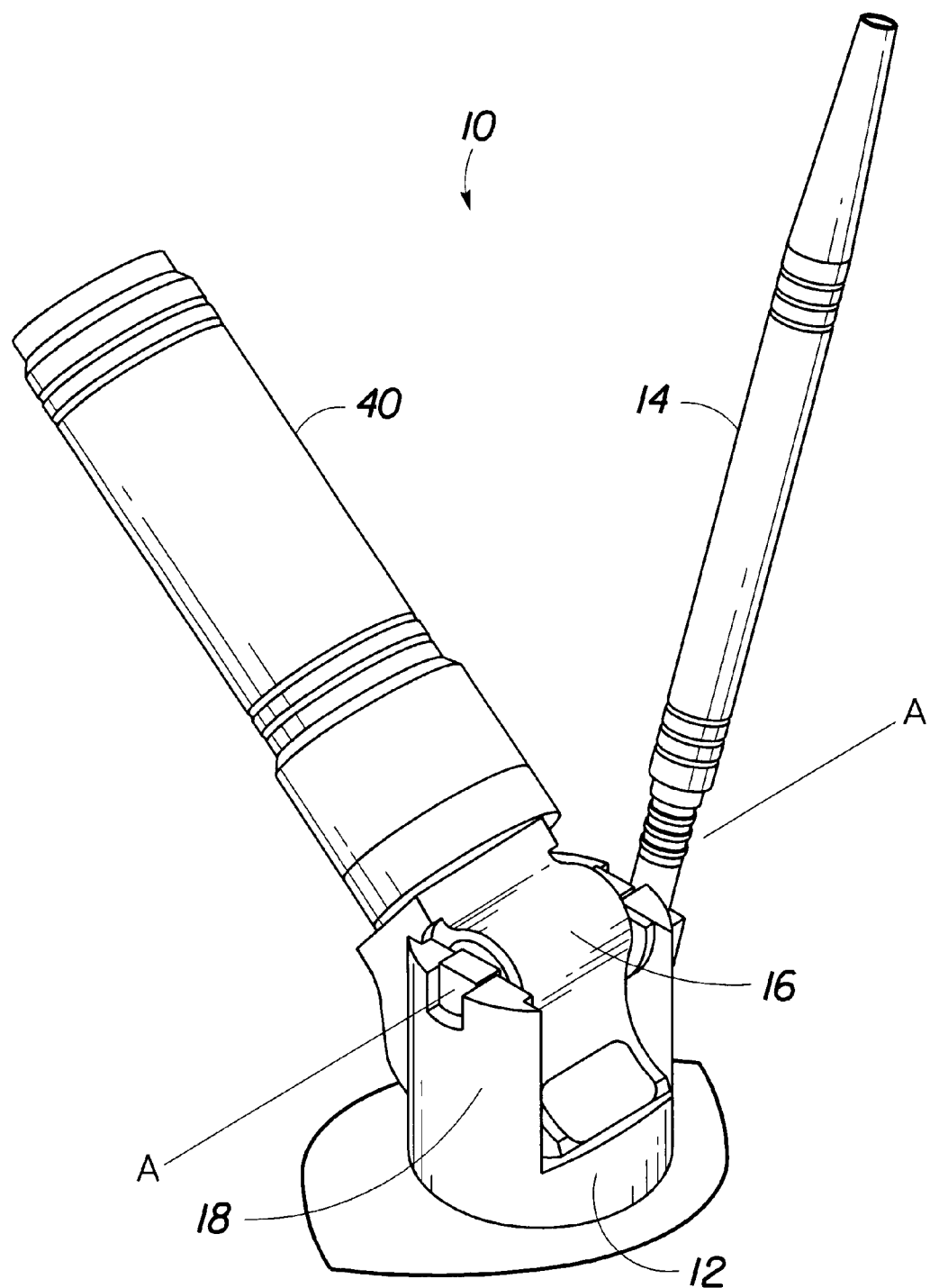
Figure 3:
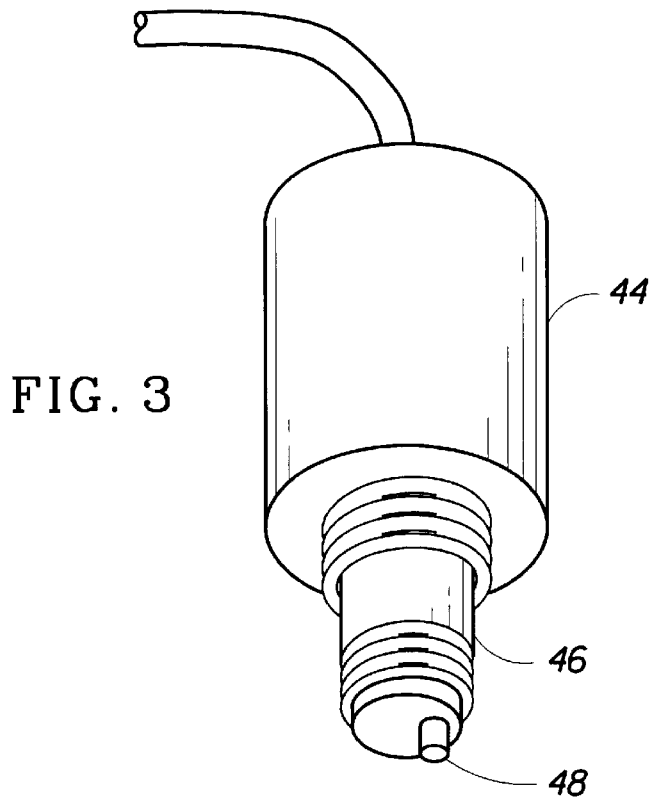
Figure 4A:
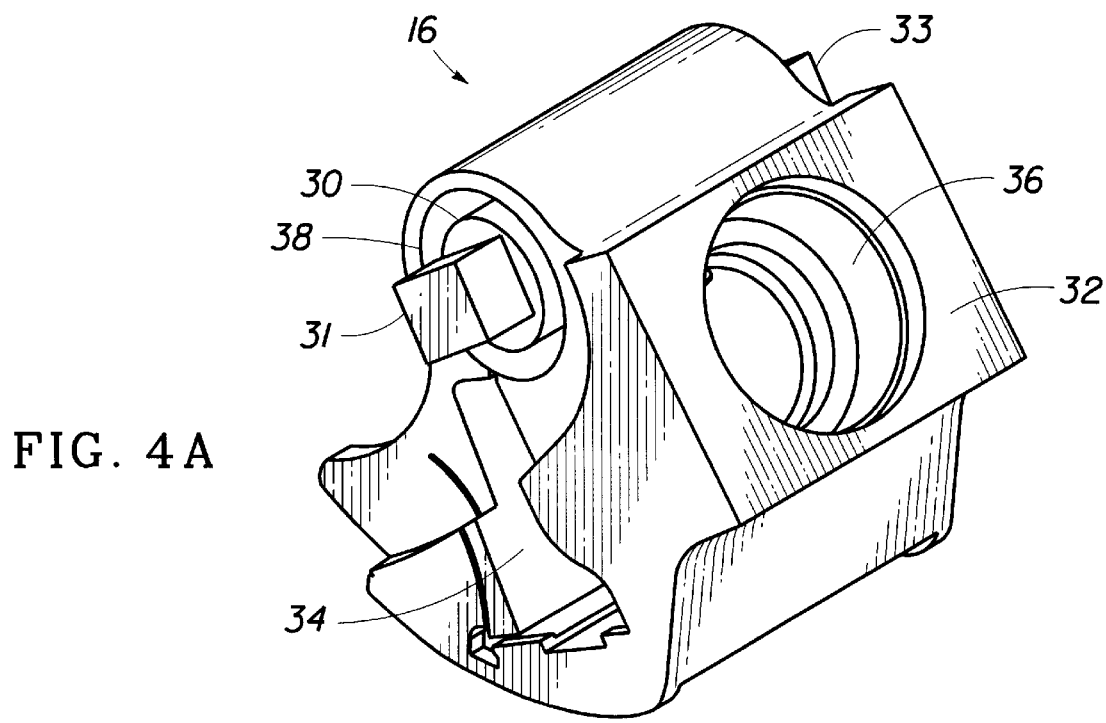
Figure 4B:
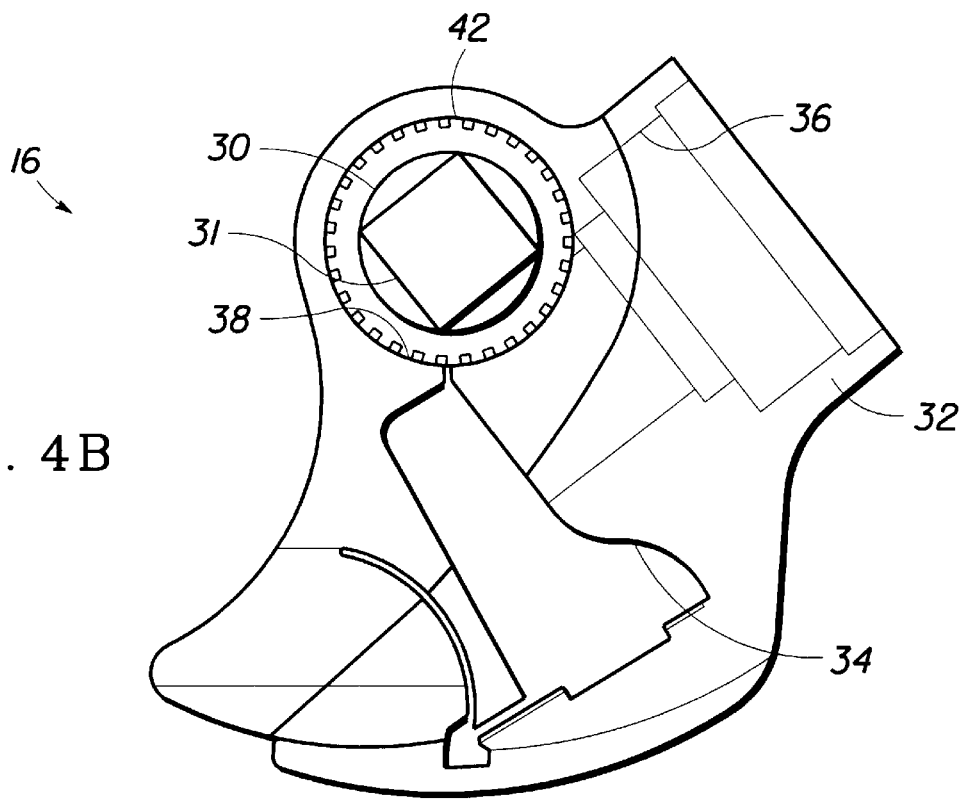
Figure 5A:
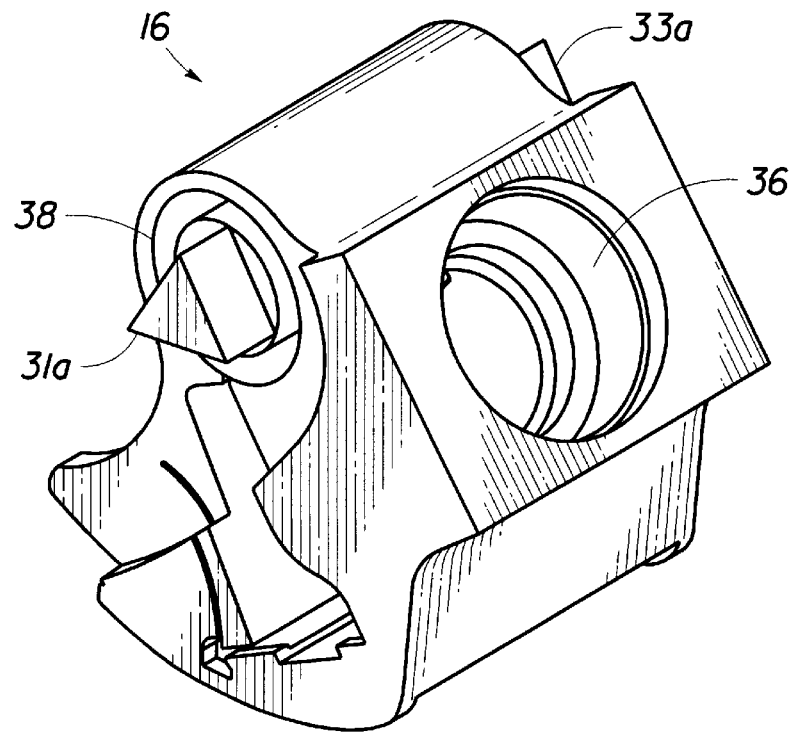
Figure 5B:
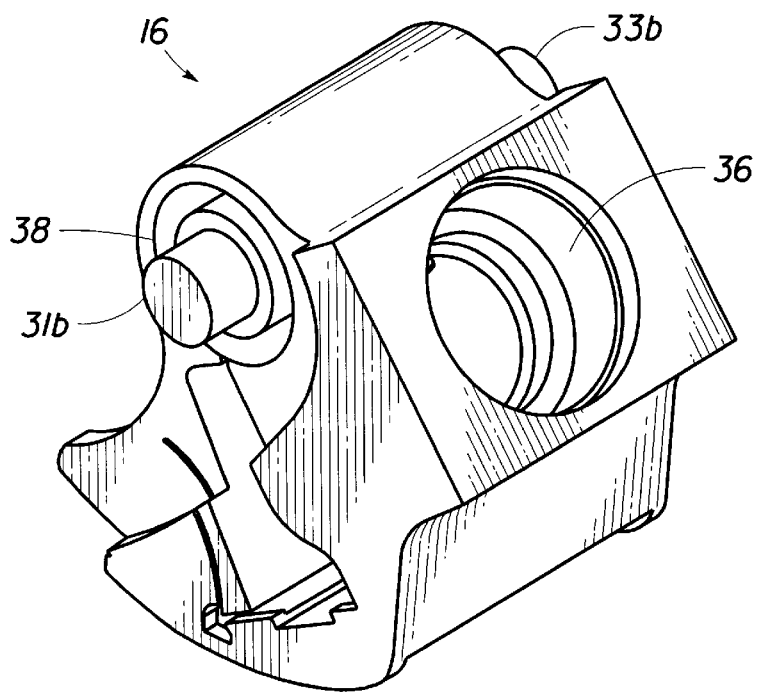
Figure 6A:
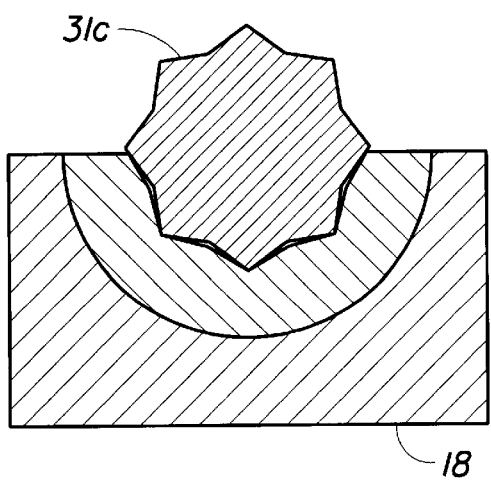
Figure 6B:
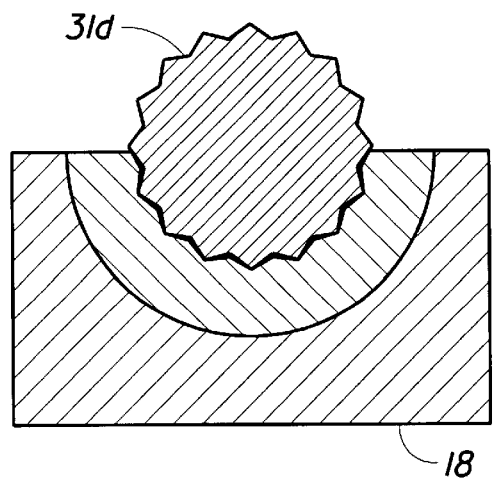
Figure 7:
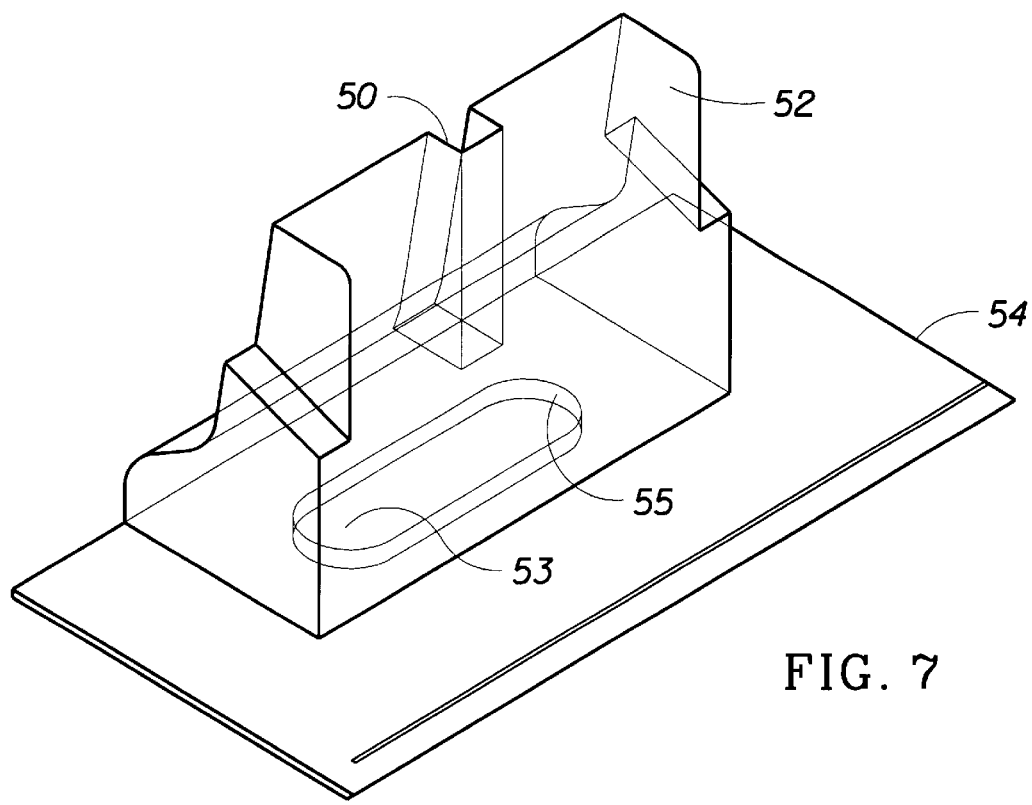
Figure 8A:
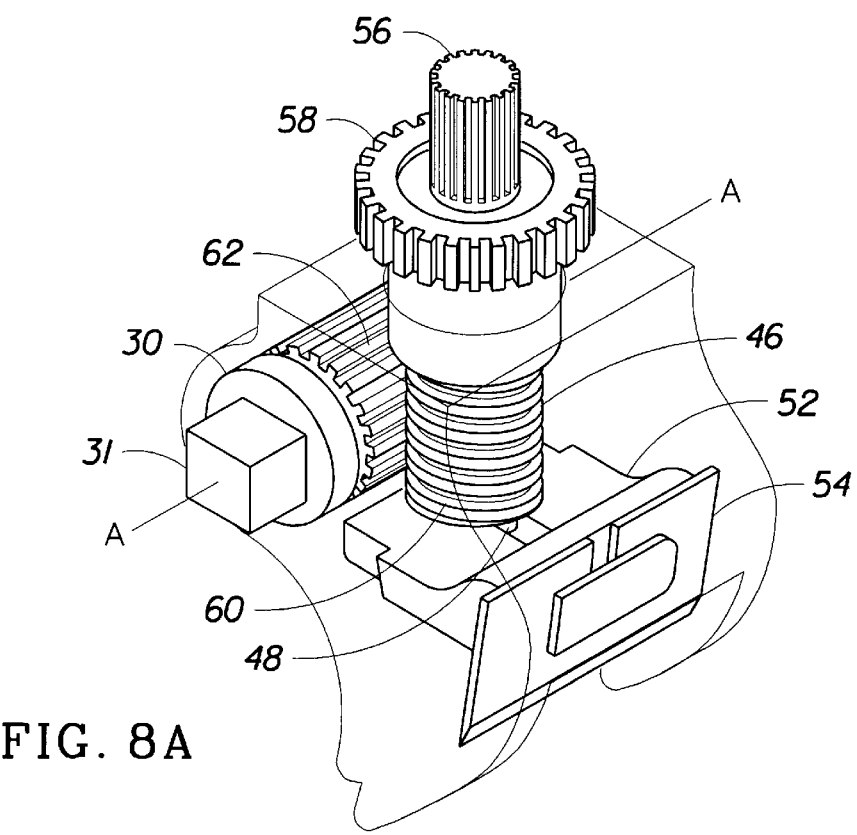
Figure 8B:
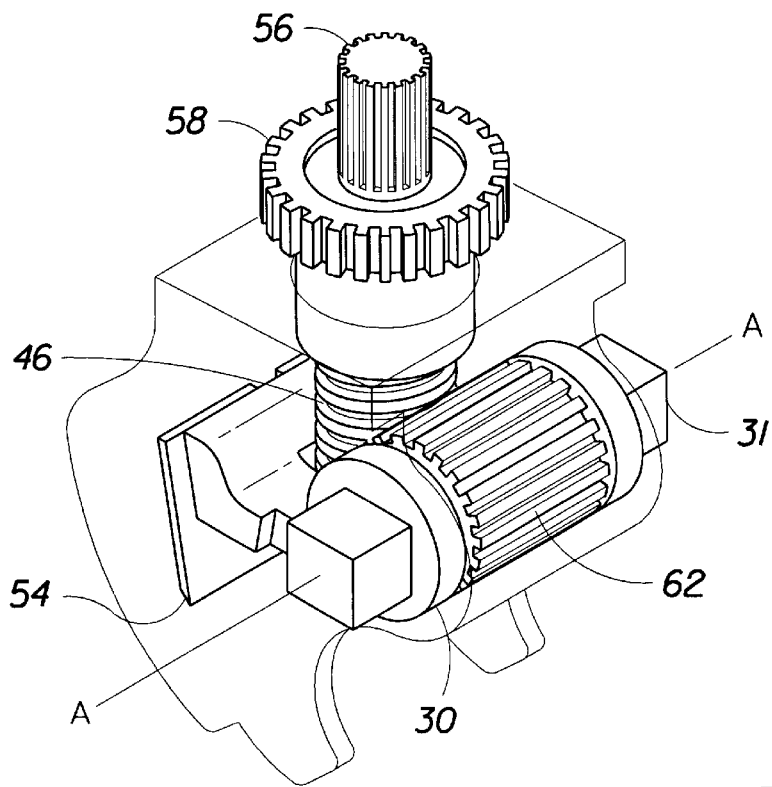
Figure 8C:
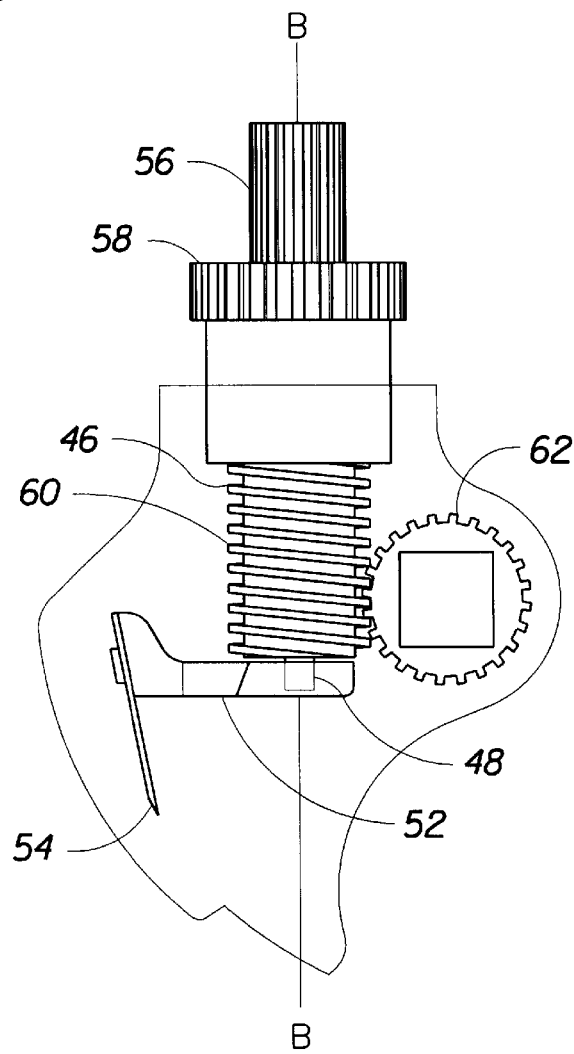
Figure 8D:
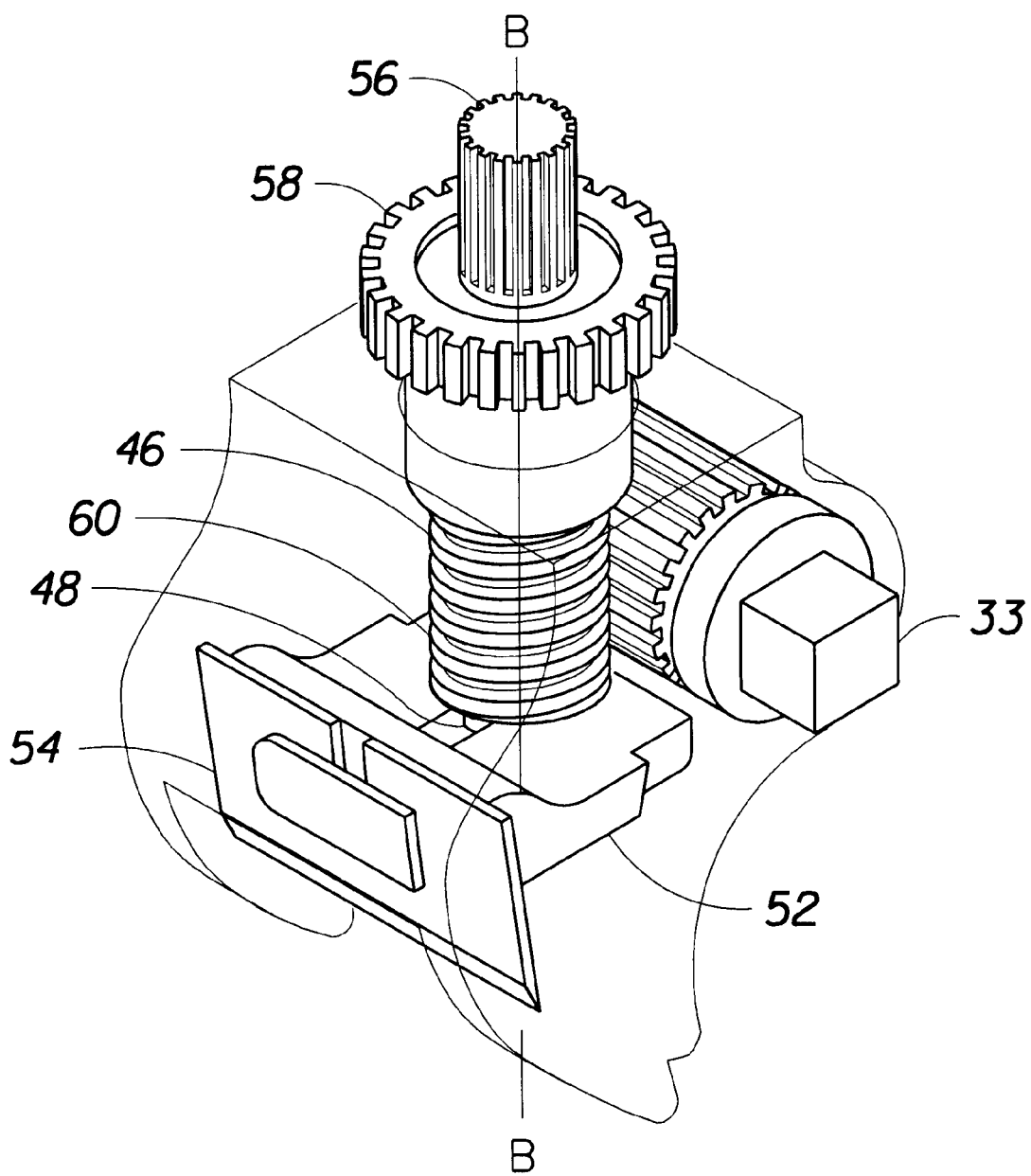
Figure 9A:
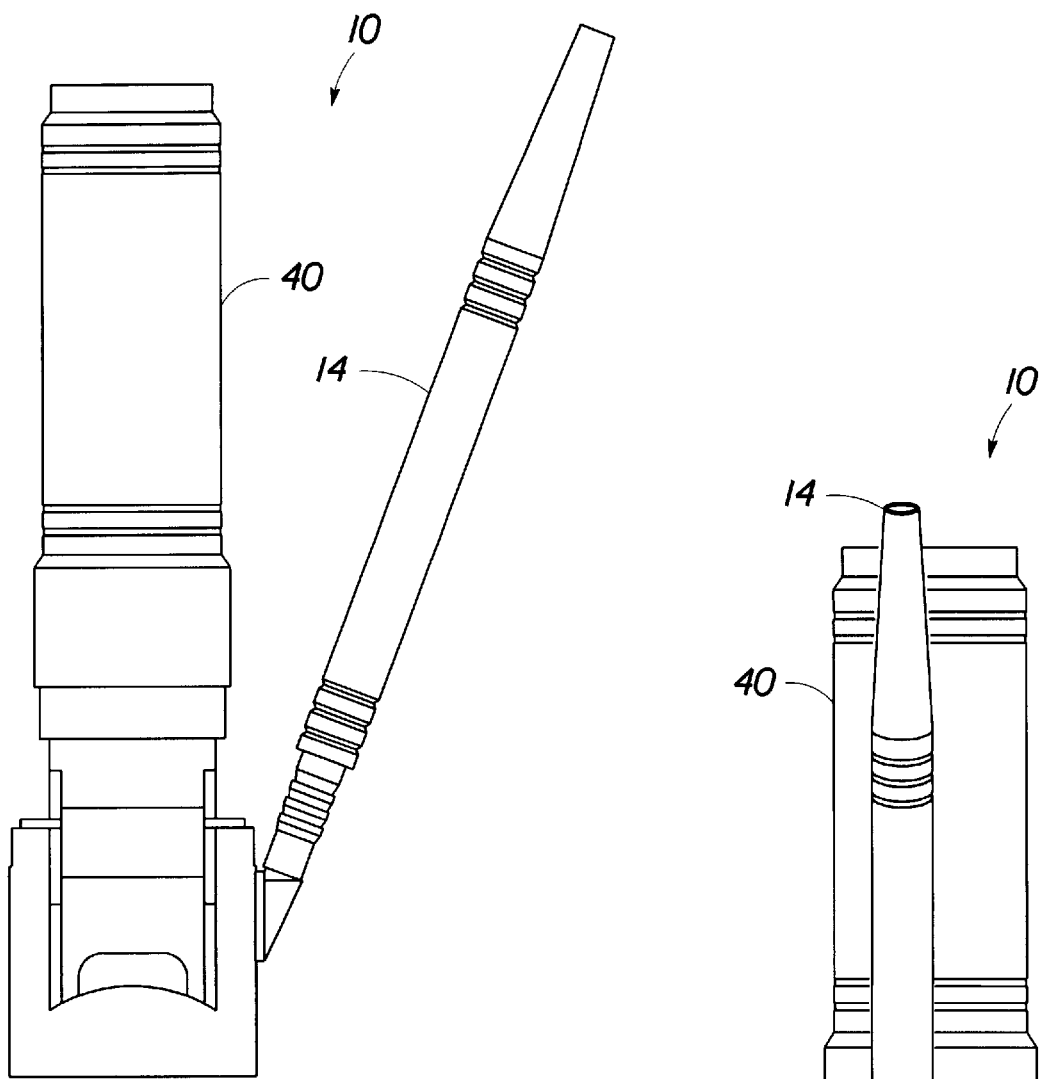
Figure 9B:
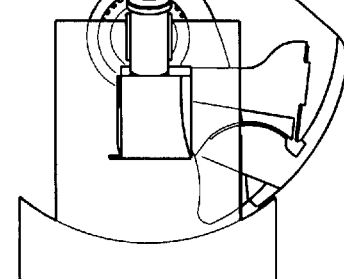
Figure 9C:
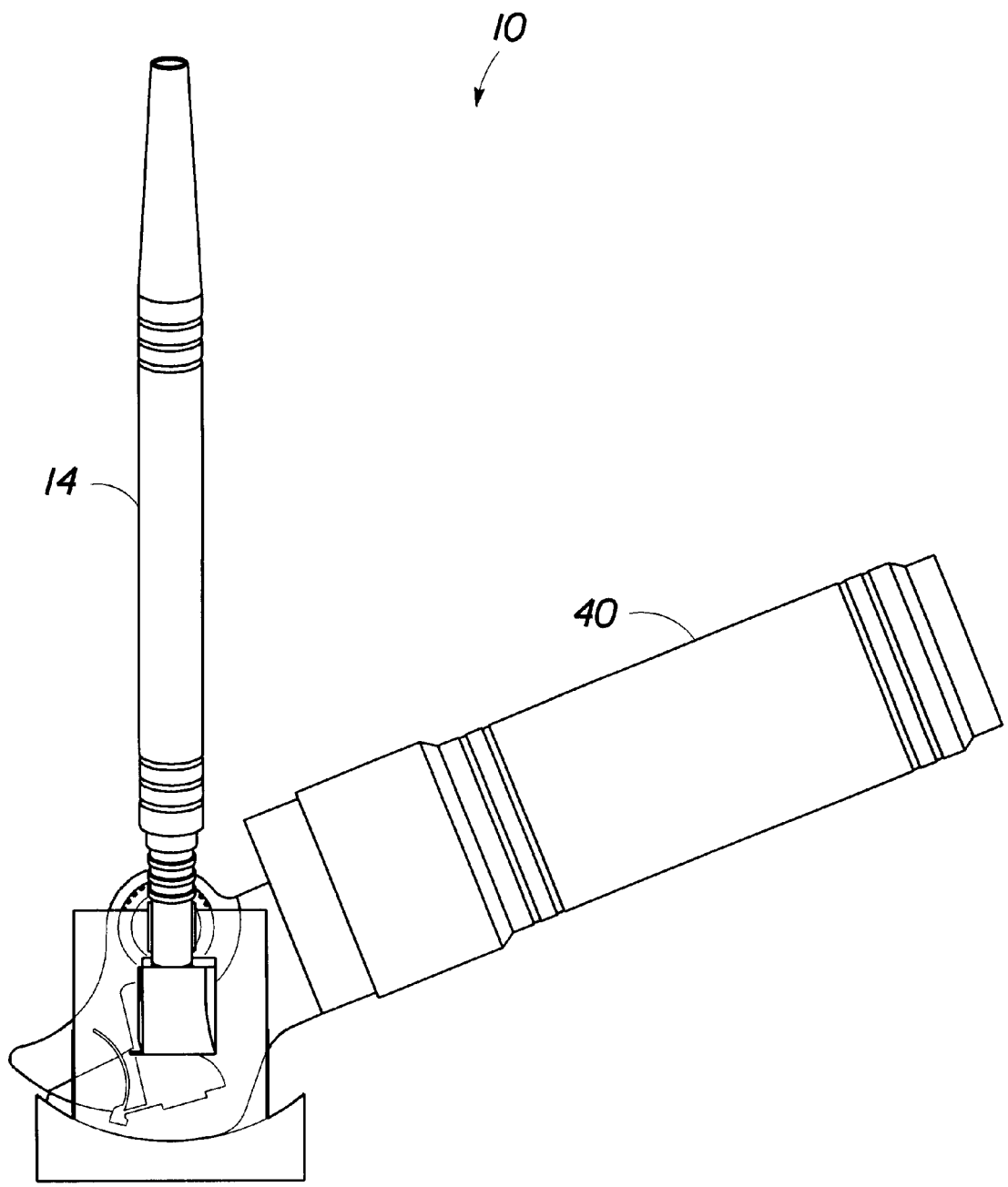
Figure 10:
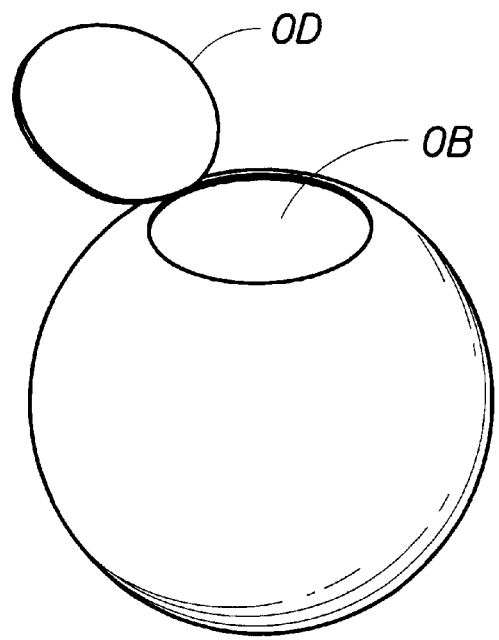
Figure 11:
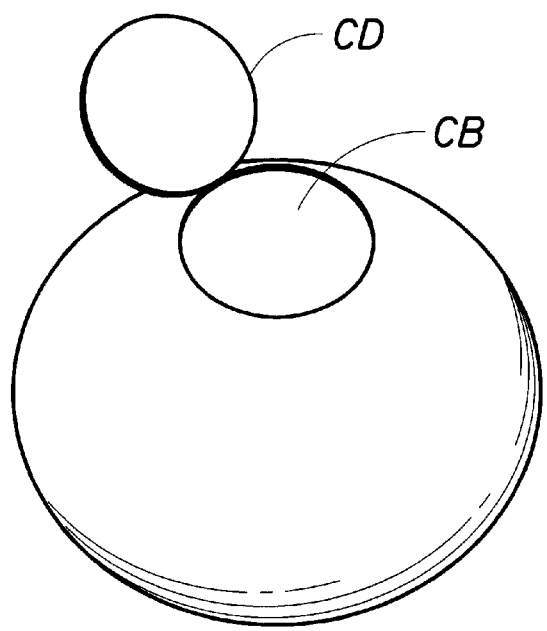
Figure 14A:
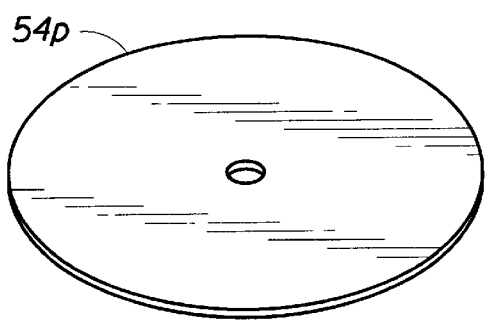
Figure 14B:
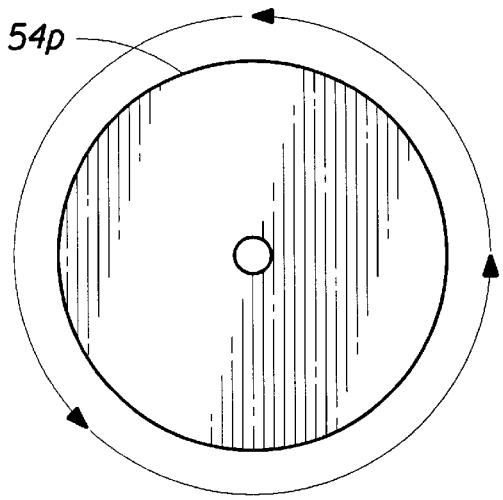
Figure 15A:
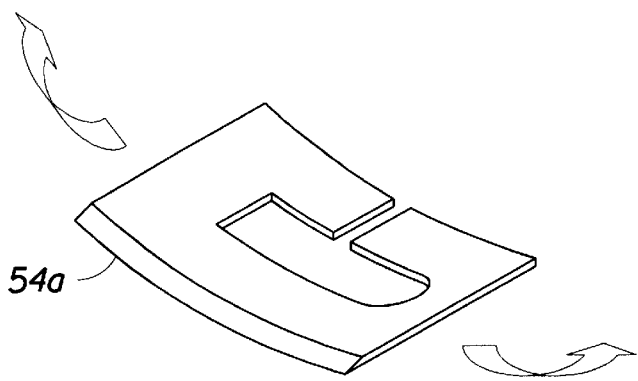
Figure 15B:
Figure 16:
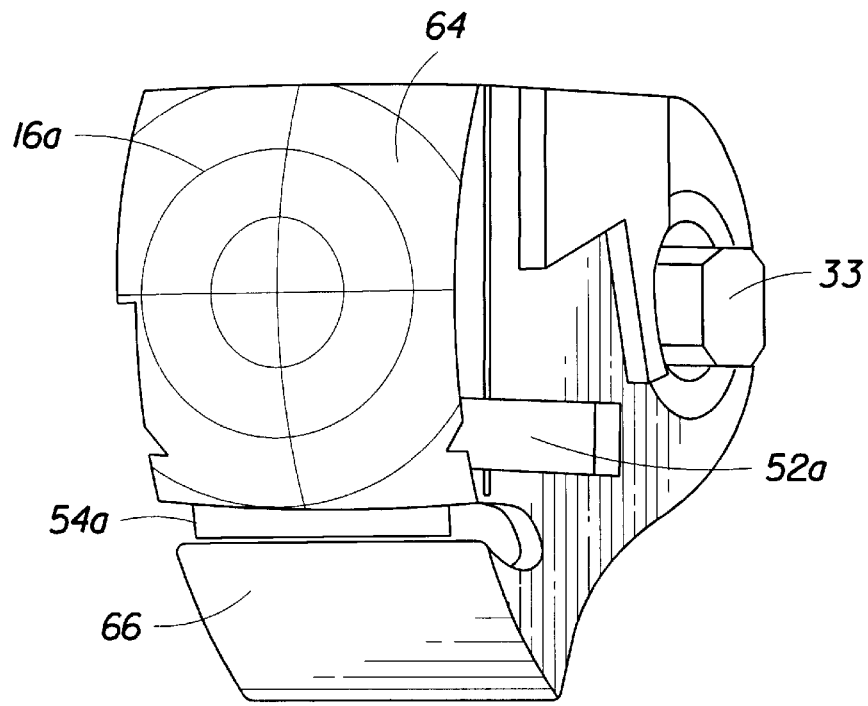
Figure 17:
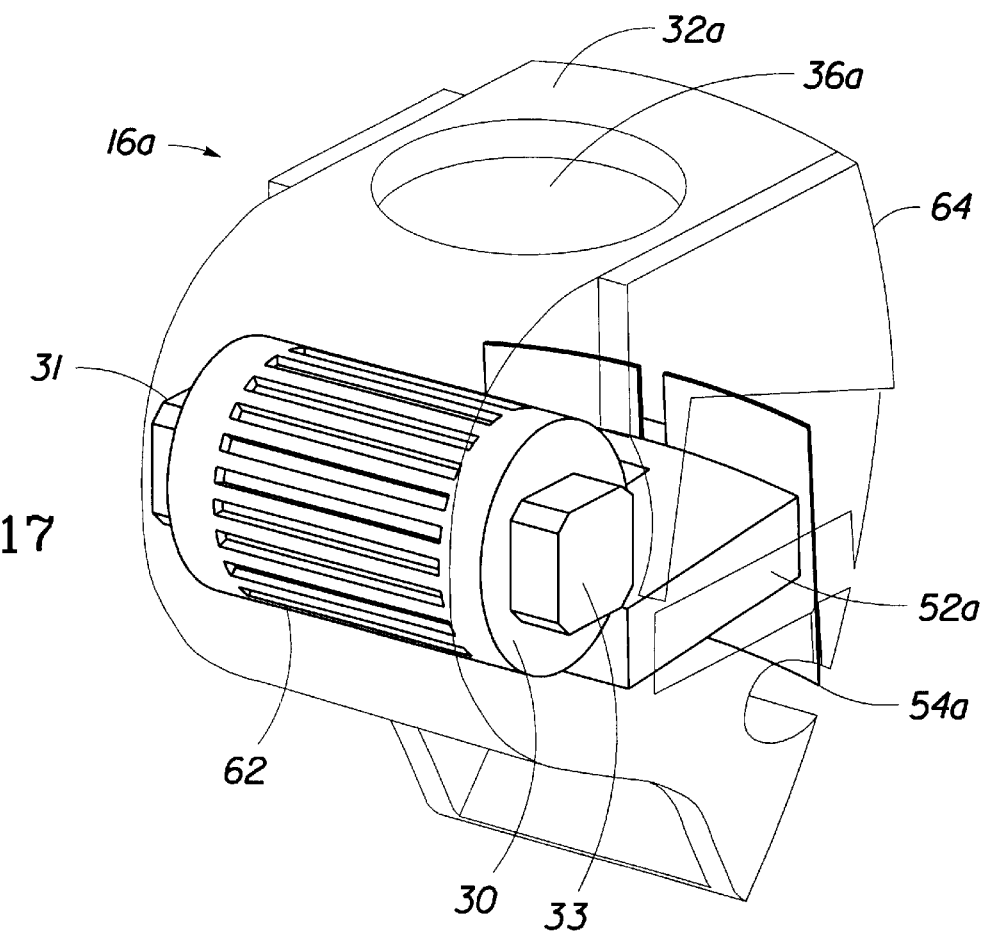
Figure 18:
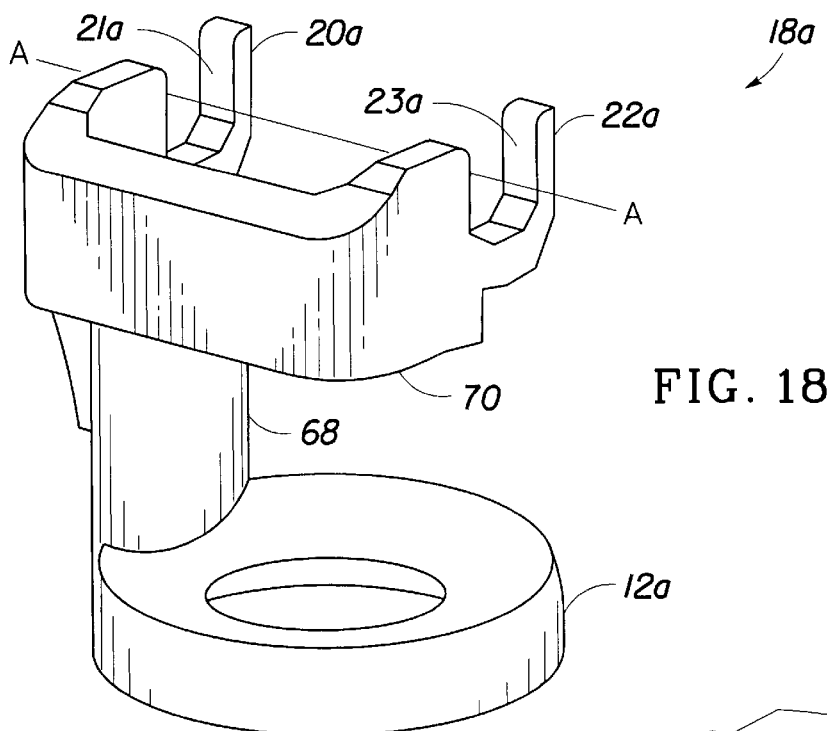
Figure 19A:
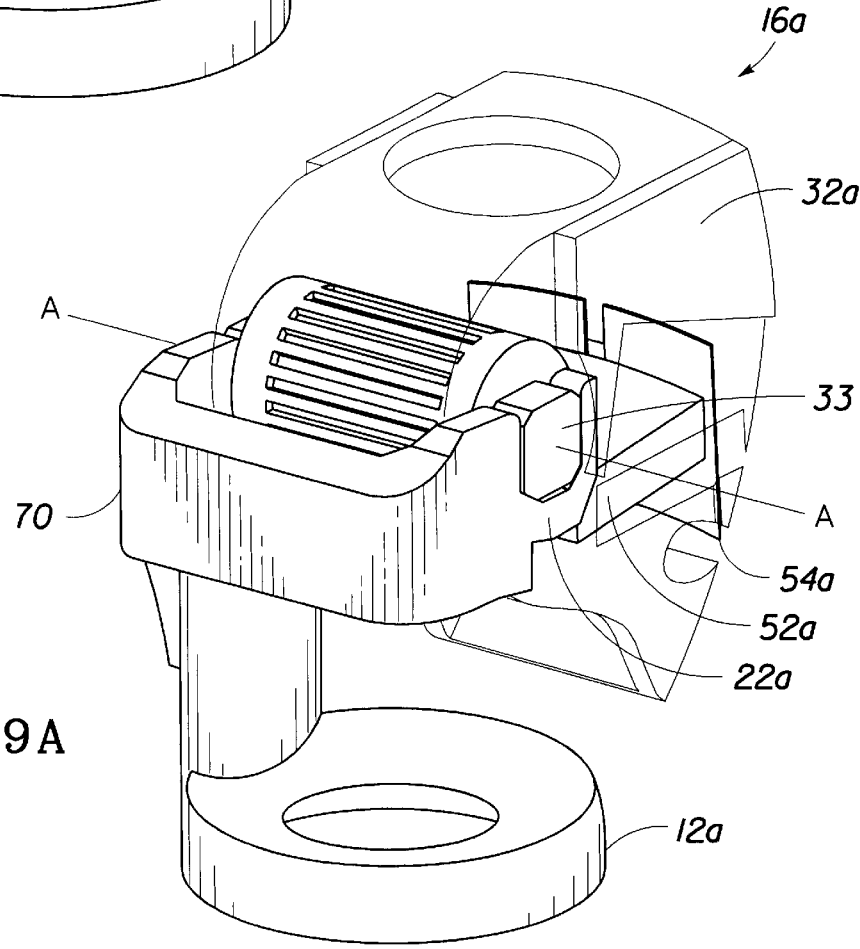
Figure 19B:
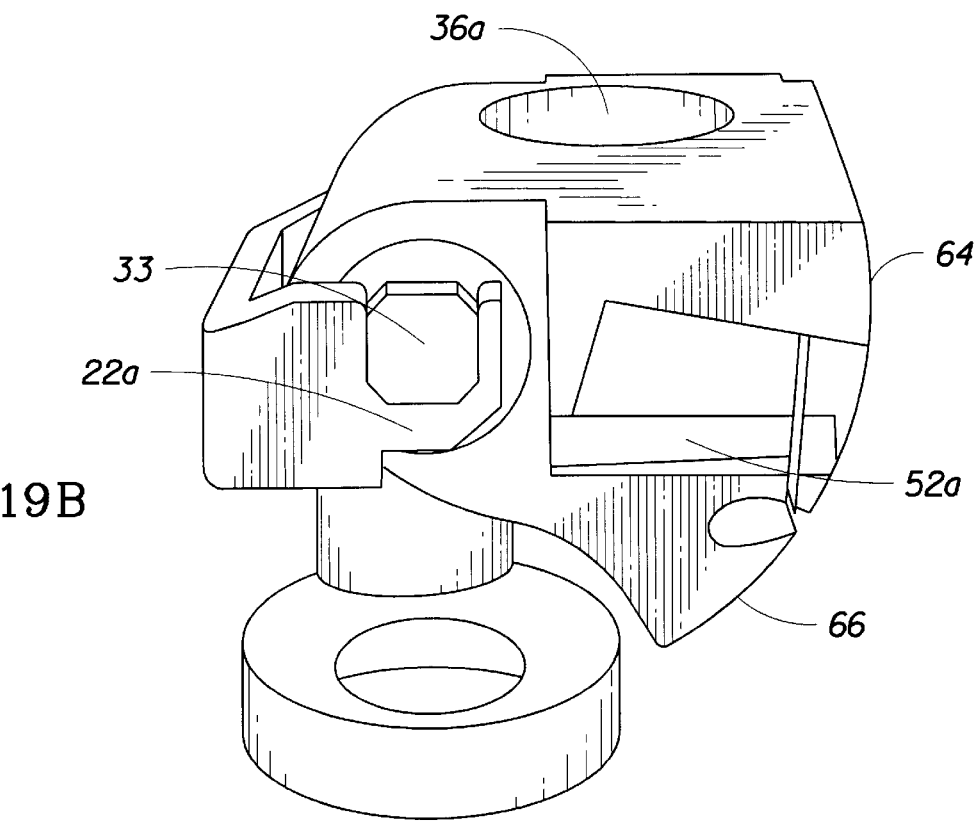
Figure 19C:
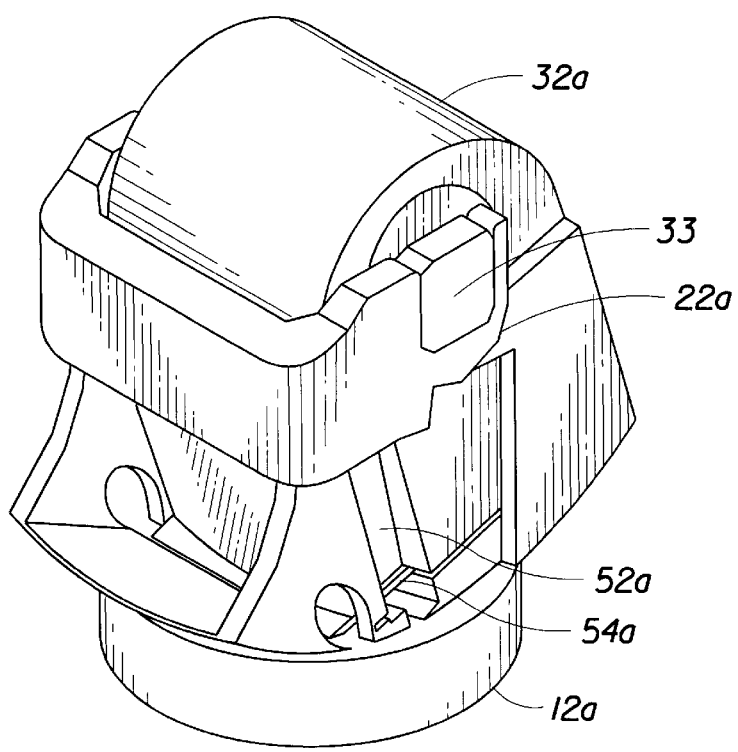
Figure 19D:
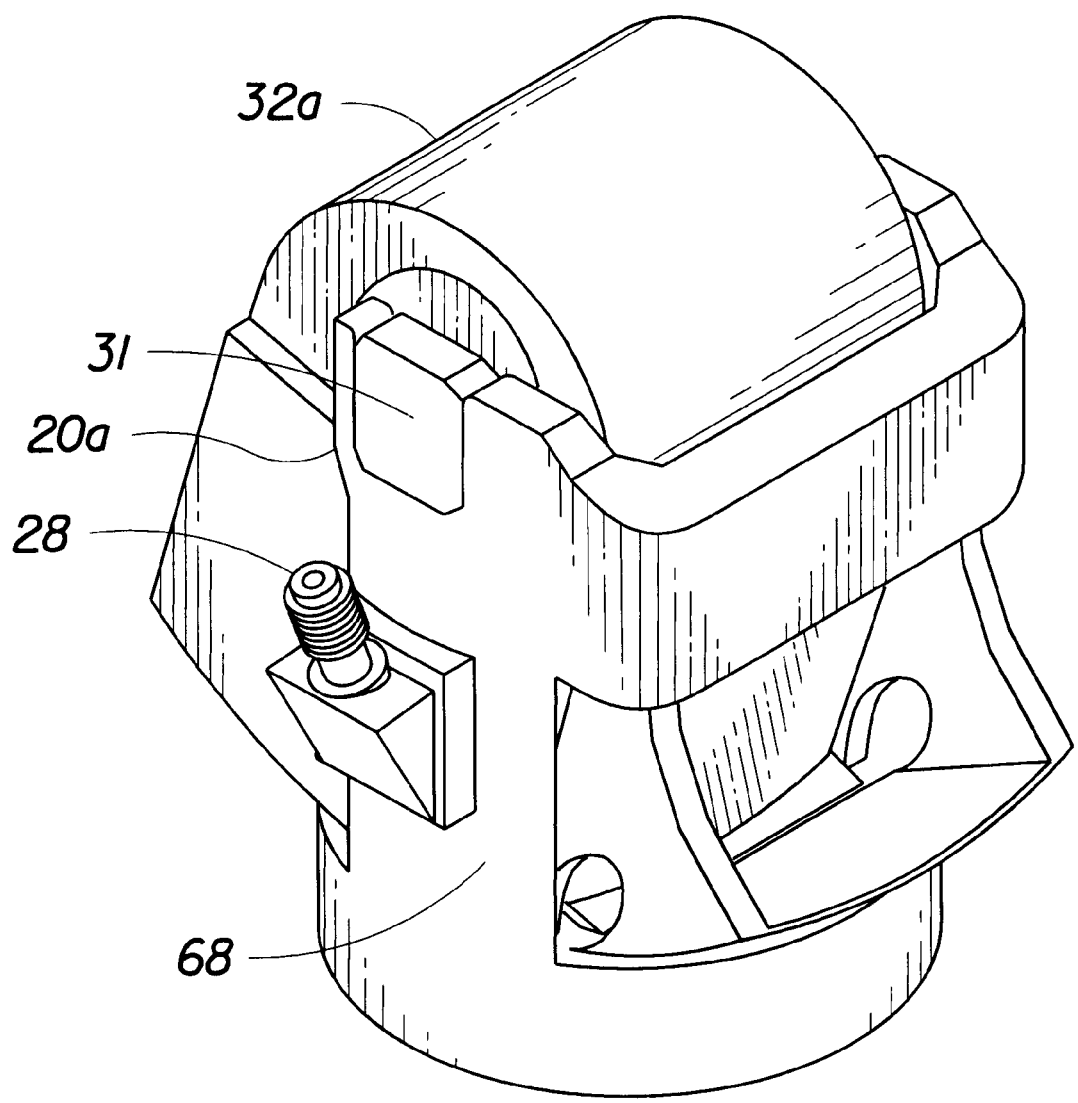

FIG. P2 is a perspective view of another prior art microkeratome;

FIG. 1 is a perspective view of a microkeratome and guide ring assembly in accordance with one embodiment of the present invention;

FIGS. 2A, 2B, 2C, and 2D are perspective, plan, frontal elevation, and side elevation views, respectively, of a vertical support assembly in accordance with the present invention;

FIG. 3 is a schematic representation of a drive motor assembly in accordance with one embodiment of the present invention;

FIGS. 4A and 4B are perspective and side elevation views of the cutting head utilized in the embodiment of FIG. 1;

FIGS. 5A and 5B are perspective views of the cutting head equipped with two alternative embodiments of a support shaft, in contrast to the support shaft shown in the cutting head of FIGS. 4A and 4B;

FIGS. 6A and 6B are side views of two additional embodiments of the cutting head support shaft;

FIG. 7 is a perspective view of a cutting blade and blade holder in accordance with the present invention;

FIGS. 8A, 8B, and 8D are perspective views, taken from different viewpoints, of the cutting head and drive gear assembly in accordance with one embodiment of the present invention;

FIG. 8C is a side view of the cutting head and drive gear assembly shown in FIGS. 8A, 8B, and 8D;

FIG. 9A is a front elevation view of one embodiment of a microkeratome and guide ring assembly in accordance with the present invention;

FIGS. 9B and 9C are side elevational views of the embodiment of FIG. 9A shown at the initial and end positions of a corneal resection;

FIG. 10 is a perspective view of a sphere representing an ocular globe with an oval-shaped disk having been cut from the upper region of the sphere;

FIG. 11 is a perspective view of a sphere representing an ocular globe with a round-shaped disk having been cut from the upper region of the sphere in accordance with the present invention;

FIGS. 12A–12C show perspective, superior, and lateral views of an arcuate cutting blade in accordance with the present invention;

FIGS. 13A and 13B show different perspective views of an arcuate cutting blade attached to a blade holder in accordance with the present invention;

FIGS. 14A and 14B are perspective and superior views of a prior art circular-shaped cutting disk;

FIGS. 15A and 15B illustrate that arcuate cutting path followed by the cutting blade in accordance with the present invention;

FIGS. 16 and 17 are posterior and anterior perspective views of a cutting head, blade holder, and arcuate cutting blade in accordance with the present invention;

FIG. 18 is a vertical support assembly in accordance with the present invention;

FIGS. 19A–19C are perspective views showing the sequential movement of the cutting head, blade holder, and arcuate cutting blade through its arcuate cutting stroke; and FIG. 19D is a perspective view shown from the reverse angle of the perspective view shown in FIG. 19C.

DETAILED DESCRIPTION OF THE PREFERRED EMBODIMENTS

FIGS. 1–9D illustrate various embodiments of a microkeratome for performing a lamellar keratotomy or a lamellar keratectomy of an ocular globe, in accordance with the present invention. The instrument is suitable to perform surgery of myopia (nearsightedness), hyperopia (farsightedness), astigmatism and presbyopia (corneal stiffening due to aging), and is particularly well-suited to perform cuts other than temporo-nasal, such as bottom, upper, and oblique cuts.

With reference first to FIG. 1, microkeratome 10 generally includes guide ring assembly 12 adapted for placement directly on a patient's eye or ocular globe such that the globe's cornea protrudes therethrough. Means, including suction conduit 14, are provided for temporarily fixing guide ring 12 to the ocular globe. Cutting head 16 containing a cutting blade suitable for corneal resections is also provided, and will be discussed in greater detail below. Vertical support assembly 18 is connected to, or alternatively forms a part of, guide ring 12 and supports cutting head 16 for rotation about horizontal axis A—A elevated above guide ring 12 such that rotation of cutting head 16 about horizontal axis A—A moves a cutting blade (described below) along an arcuate cutting path into engagement with the cornea of the patient's ocular globe.

FIGS. 2A–2D illustrate guide ring 12 and vertical support assembly 18 in greater detail. Thus, vertical support assembly 18 includes a pair of arm members 20, 22 extending upwardly from guide ring 12 and spaced 180° apart from each other. By virtue of such spacing and orientation, arm members 20, 22 bound arcuate surface 24 which contains circular opening 26 permitting passage of the patient's cornea. Arm members 20 and 22 are further equipped with slots 21 and 23, respectively, for rotating cutting head 16 about axis A—A, as will be described further below.

Guide ring 12 is further equipped with vacuum adapter 28 for connection to suction conduit 14 shown in FIG. 1. The lower portion of guide ring 12 defines suction ring 13 which conducts partial vacuum (below atmospheric) pressure delivered through suction conduit 14 and vacuum adapter 28 from a vacuum pump (not shown) to the patient's ocular globe or eyeball. In this manner, the eyeball is immobilized relative to the guide ring and the intraocular pressure is regulated.

Cutting head 16 is shown in greater detail in FIGS. 4A–5B. The cutting head includes support shaft 30 which extends laterally through body 32. Support shaft 30 is equipped with lateral support members 31, 33 on either end thereof that extend from opposing sides of cutting head body 32 for engagement with slots 21, 23, respectively, of upwardly extending arm members 20, 22 of the support assembly, as seen in FIGS. 2A–2B.

Figure 2A:
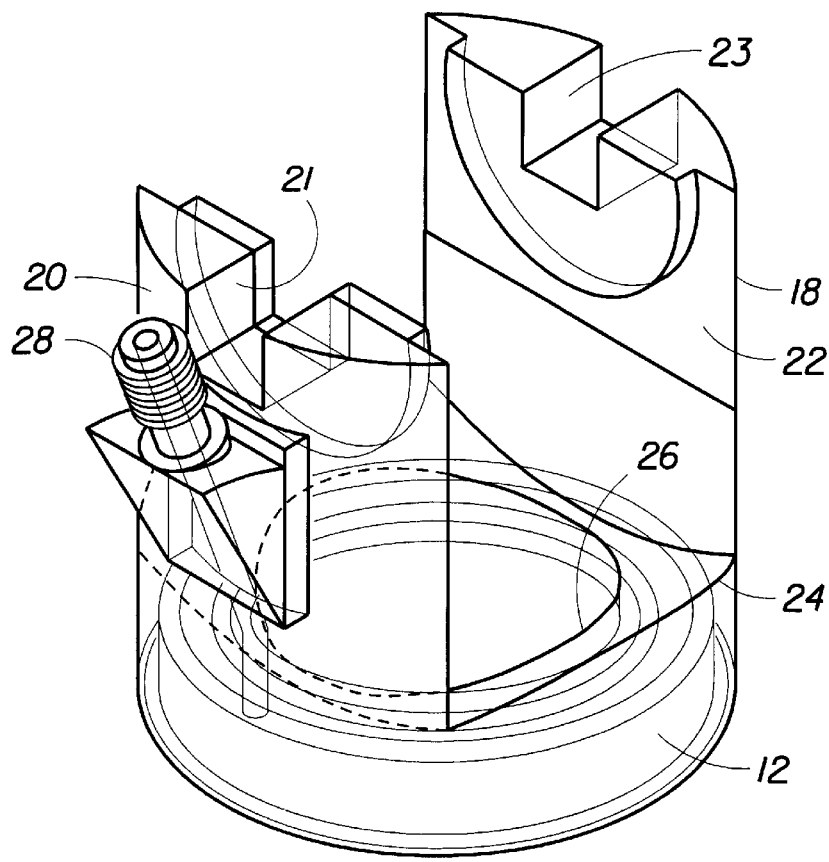
Figure 2B:
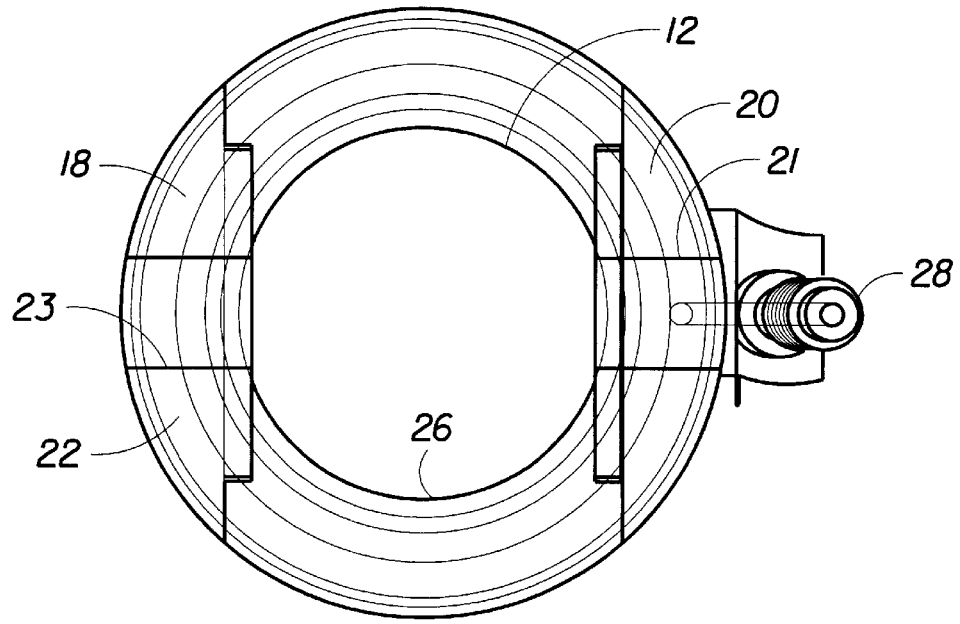
Figure 2C:
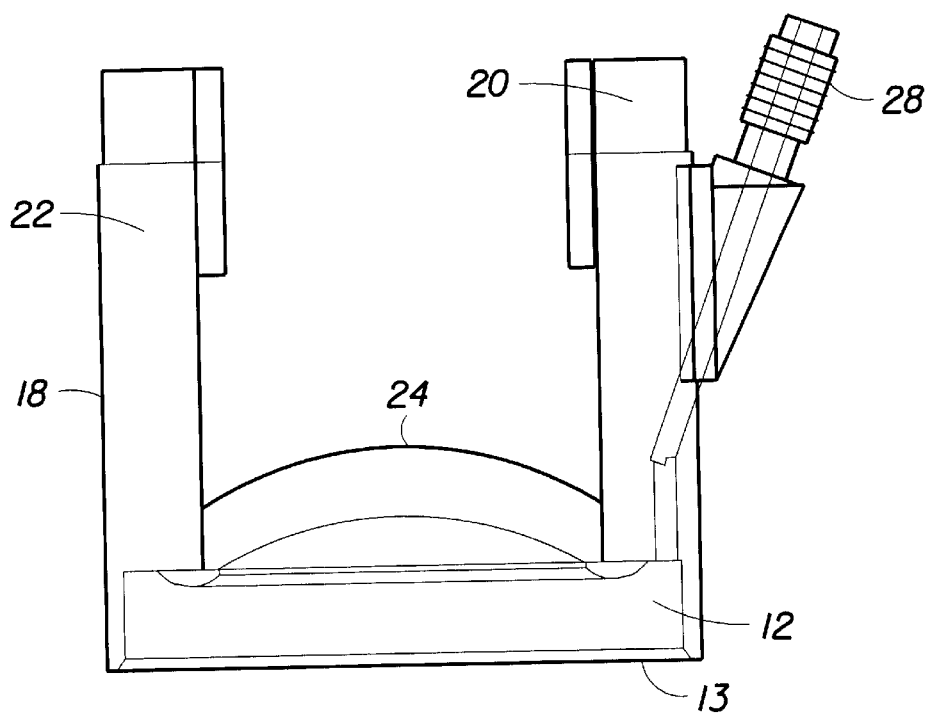
Figure 2D:
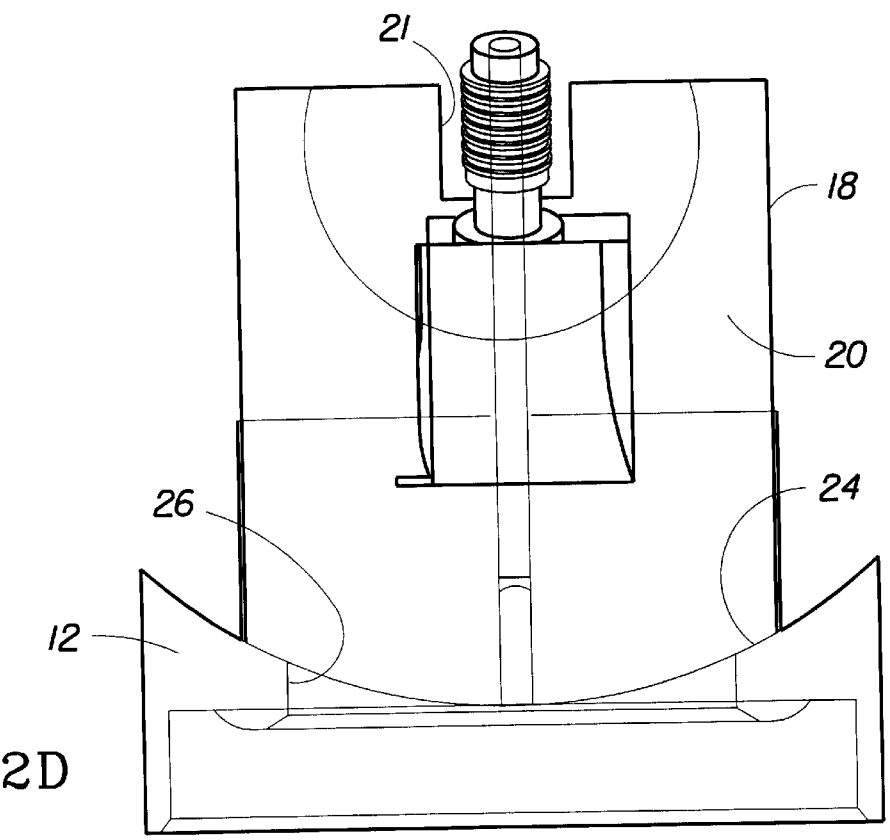

Referring back to FIGS. 4A–4B, as well as FIGS. 2A–2B, lateral support members 31, 33 of support shaft 30 are square-shaped and sized for closely fitting within U-shaped square slots 21, 23 defined by arm members 20, 22 of vertical support assembly 18. In this manner, support shaft 30 of cutting head 16 is placed in static engagement with arm members 20, 22 whereby the support shaft is constrained against rotation relative to vertical support assembly 18 and guide ring 12.

FIG. 5A illustrates an alternative embodiment wherein support shaft 30 terminates in triangular-shaped lateral support members 31a, 33a for static engagement (not shown) with the upwardly extending arm members of the vertical support assembly. Those skilled in the art will appreciate that the arm members of this embodiment will define V-shaped slots sized for a close fit with support members 31*a,* 33*a.*

FIG. 5B illustrates another alternative embodiment wherein support shaft 30 terminates in circular-shaped lateral support members 31*b,* 33*b* for rotational engagement (not shown) with the upwardly extending members of the vertical support assembly whereby the support shaft is free to rotate relative to the upwardly extending arm members. In this embodiment, the arm members will define semi-circular openings for a close fit with support members 31*b,* 33*b.*

The embodiment of cutting head body 32 shown in FIGS. 4A–5B is a uni-body of cast construction having a side opening therein for moving a blade and blade holder assembly through cavity 34. In addition to cavity 34, cutting head 32 includes substantially cylindrical opening 36 of variable bore size and depth, as well as lateral cylindrical bore 38 therein. Opening 36 is formed with either threads or a mechanical slot for engagement with complementary threads or mechanical key on handle 40 (see FIG. 1) of microkeratome 10. The action of a drive motor carried within handle 40 in one embodiment of the present invention will be explained below.

Lateral bore 38 is sized for accepting shaft 30 having outer threads 42, or alternatively mechanical teeth 42, and support members 31, 33, which are square-shaped as indicated in FIGS. 4A and 4B. These support members may alternatively be triangular as seen at 31*a* and 33*a* in FIG. 5A, circular as seen at 31*b* and 33*b* in FIG. 5B, or star-shaped as seen at 31*c* and 31*d* in FIGS. 6A and 6B.

The cutting head may be further equipped with upper and lower portions connected by a hinge (not shown) that permits the cutting head to be opened for accessing the cutting blade. Alternatively, the cutting head may be equipped with first and second laterally connected portions for the same purpose.

Microkeratome 10 further includes means for rotating cutting head 16 about elevated horizontal axis A—A to move the cutting blade at least partially through the cornea to create a corneal flap during a lamellar keratotomy. The rotating means includes, in at least one embodiment of the present invention, means for inducing oscillatory motion in the cutting blade of the cutting head that is transverse the cutting path defined by rotation of the cutting head about the elevated horizontal axis.

With reference now to the schematic representation of FIG. 3, electric drive motor 44, or other similar means provides the torque necessary for rotating input shaft 46, which terminates outside the motor housing in small eccentric projection or pin 48. As indicated by the gear arrangement shown in FIGS. 8A and 8B, torque from drive motor 44 is applied to shaft 46 to effect a desired rotation speed of cutting head 16, as will be explained below, as well as to rotate pin 48. The assembly of drive motor 44 and input shaft 46 is mounted within handle 40 in such a manner that, when handle 40 is engaged with cutting head 16, eccentric pin 48 engages slot 50 of blade holder 52, seen in FIG. 7, to transmit an oscillatory motion to blade 54 that corresponds to the speed of the motor. This arrangement of blade holder 52, blade 54, and eccentric pin 48 is shown in FIGS. 8A–8D.

Cutting blade 54 is rectangular and includes elongated slot 55 that closely fits over projection 53 of blade holder 52 to mount the blade to the blade holder within the cutting head. As mentioned above, blade holder 54 has vertical rectangular groove 50 therein for engagement by eccentric pin 48 of shaft 46 through cylindrical cavity 36 of the cutting head. As the eccentric pin is rotated off-center by shaft 46, it induces back-and-forth lateral motion of blade holder 52 within cavity 34 of the cutting head. This lateral motion results in the oscillation of blade 54.

Rotation of input shaft 46 also rotates external threads 60 thereon about axis B—B, which, in the embodiment of FIGS. 8A–8D, induces rotation of cutting head 16 about axis A—A. More particularly, threaded portion 60 of shaft 46 engages outer threads 62 of shaft 30. Since shaft 30 is constrained against rotation by the engagement of support members 31 and 33 in openings 21 and 23, respectively, of support assembly 18, the torque of input shaft 46 induces the input shaft, motor 44, handle 40, and cutting head 16 to all rotate as a unit about axis A—A. In this manner, the cutting blade (described below) cuts at least partially through the cornea to perform the desired lamellar keratotomy.

Threaded sections 60 and 62 may be of various diameters so as to provide for speed adjustments therebetween, in other words, step-down, step-up, or constant speed, between the rate of blade oscillation and the rate of cutting head rotation about axis A—A. Thus, these rates may be 1:1, or the speed of the blade oscillation may be designed to be faster or slower than the speed of cutting head rotation about axis A—A. Alternatively, gears 56, 58 mounted to shaft 46 may be utilized for such speed control purposes.

If support shaft 30 is instead free to rotate relative to upwardly extending members 18, as in the embodiment of FIG. 5B, the means for rotating cutting head 16 will include a handle (not unlike handle 40) connected to the cutting head, which is adapted for gripping by a surgeon to manually induce rotation of the cutting head about the elevated horizontal axis. Those skilled in the art will appreciate that this manually driven embodiment can also be equipped with drive motor 44 for inducing the transverse oscillatory motion of blade 54 as the blade is moved through the cornea. Such oscillatory motion promotes a smooth, continuous cut through the corneal tissue.

The microkeratome may further include a stop means (not shown) for limiting the range through which the cutting blade is carried by said cutting head so as to define a corneal hinge during a lamellar keratotomy. For example, when a portion of the cutting head collides with the stop means, the increased load applied to drive motor 21 will trigger a control circuit to stop and/or reverse the direction of motor 21 as desirable for completing the lamellar keratotomy.

The microkeratome may also be equipped with an adjustable float head (not shown) connected to the cutting head for at least partially compressing the cornea ahead of the cutting blade so as to set the corneal resection to the desired shape and thickness. The adjustable float head preferably includes a pair of substantially parallel float arms, and a float having a multi-sided cross-section with multiple respective faces and being supported for rotation between the float arms about a journal that extends through the float. The float head may be equipped with indicia thereon for indicating the resection thickness provided by the selected face.

It is further preferred that each of the faces of the float be spaced at different distances from the journal, whereby the thickness of the corneal resection is varied by rotation of the float until the desired face is in position to compress the cornea. The float may be equipped in various ways, such as by having at least one arcuate face and/or one oblique face, whereby different corneal lenticular resections are performed by compressing the cornea with the respective face. The structure of the float head assembly is described more completely in U.S. Pat. No. 5,980,543, the entire contents of which are incorporated herein by reference.

Those skilled in the art will appreciate that the present invention will permit the orientation of microkeratome 10 in any direction without colliding with the annexes of the eye. The cutting head assembly permits cutting blade 54 to be moved beneath a cutting plane that would be defined by the upper surface of a typical flat-disc type guide ring. The vertical support assembly also dispenses with the need for a larger surface area required by those systems incorporating external drive gear assemblies. Since microkeratome 10 makes use of only one internal gear system, it requires only a minimum available surface area about the patient's cornea. Thus, the present invention is capable of cutting in all directions because the apparatus has the capacity to cut without surpassing the borders of the guide ring assembly.

A surgical procedure is initiated by placing suction ring 13 on the ocular globe in the desired cutting orientation. A vacuum pump (not shown) is activated to attract the cornea to concentric hole 26 of the suction ring at an appropriate pressure to maintain the cornea in a fixed position during the cut. At that time, the lateral support members of shaft 30 are introduced inside the upper slots defined by arm members 20, 22 of vertical support assembly 18, as shown in FIGS. 9A–9B.

Activation of motor 44 advances the instrument so as to first perform a partial flattening of the cornea and then cut the corneal disk as indicated by the sequence of FIGS. 9B–9C. When cutting head 16 collides with a stop means (not shown), the collision produces a voltage drop, triggering a reverse of the current polarity in the motor circuit, and the return of the microkeratome to its place of origin on the guide ring assembly.

It has recently been observed that the use of a flat, rectangular-shaped cutting blade such as blade 54 produces an oval-shaped corneal disk such as that shown at OD in FIG. 10. This produces certain advantages, such as allowing ablation on astigmatisms in a longer meridian. However, there are also disadvantages in an oval-shaped corneal disk, such as the fact that a hinge can only be left in the shortest meridian, which requires that larger disks be cut to account for certain ablations. Thus, in many instances, a circular-shaped disk as shown at CD in FIG. 11 is desirable because it exposes a circular corneal bed CB (FIG. 11) rather than an oval corneal bed OB (FIG. 10).

The solution for reliably producing a circular corneal cut is to equip microkeratome 10 with an arcuate cutting blade, as seen at 54a in FIGS. 12A–12C. The cutting blade may include a substantially rectangular plate having one of its edges 80 sharpened for cutting. In a preferred embodiment, the plate has a smooth, continuous bend therein making the cutting edge arcuately shaped, as seen particularly in FIGS. 12C and 15B. The cutting blade preferably includes steel, and may comprise a stainless steel alloy. An opening 53a is provided in the plate of cutting blade 54a for engagement by projection 53a of blade holder 52a. The engagement of blade holder 52a and arcuate cutting blade 54a is shown in FIGS. 13A and 13B.

FIGS. 14A and 14B are perspective and superior views of circular-shaped cutting disk 54p which was also experimented with, and was found to provide some utility, but was not found to be superior to the design of arcuate blade 54a. The use of cutting disk 54p requires a modification of the drive assembly (not shown) so that the disk is rotated, as indicated by the arrows in FIG. 14B, rather than being reciprocated across cutting head 16 like blades 54 and 54a.

It should be noted that the path of reciprocation for blade 54a is arcuately shaped like that blade, as indicated by the arrows in FIGS. 15A and 15B, and is facilitated to some extent by the inner arcuately-shaped face of planar member 64, seen in FIG. 16.

FIGS. 16 and 17 are posterior and anterior perspective views of cutting head 16a, blade holder 52a, and arcuate cutting blade 54a in accordance with the present invention. Support shaft 30 extends laterally through cutting head body 32a and terminates in support members 31, 33. Gear 62 is mounted about the central portion of support shaft 30 within cutting head body 32a, as seen particularly in FIG. 17.

FIG. 18 illustrates an alternative vertical support assembly 18a which is connected to guide ring 12a and includes a pair of U-shaped members 20a, 22a extending upwardly from the guide ring. The U-shaped members are separated 180° apart from each other by lateral support arm 70, and are elevated above guide ring 12a by vertical support arm 68 that extends upwardly from guide ring 12. Alternatively, U-shaped members 20a, 22a may extend directly upwardly from the guide ring (not shown) 180° apart from each other.

With reference now to FIGS. 19A–19D, vertical support assembly 18a supports cutting head 16a for rotation about horizontal A—A axis such that rotation of the cutting head about the horizontal axis moves cutting blade 54a along an arcuate cutting path into engagement with the cornea of the ocular globe, whereby the arcuate cutting edge of the cutting blade cuts a substantially rounded corneal disk. The movement of cutting head 16a and arcuate blade 54a through the arcuate cutting path is seen through the progression between FIG. 19B and FIG. 19C thereby. FIG. 19D is a perspective view shown from the reverse angle of the perspective view shown in FIG. 19C. Thus, cutting blade 54a is moved out of the page and to the left in the perspective of FIG. 19C, and left and into the page in the perspective of FIG. 19D.

Those skilled in the art will further appreciate that, by selective design of the curvature of the arcuate cutting edge, cutting blade 54a may also be used to produce a substantially oval-shaped corneal disk. This type of oval-shaped disk is also achievable with cutting blade 54 having the straight cutting edge, as described above, and may be selectively used to provide certain advantages in corneal resections.

Studies have shown that superior, horizontal corneal "hinges," which are achievable through the present invention, are much less likely to experience ablation and traumatic displacement following surgery than a conventional, vertical nasal hinge. Thus, a nasal hinge cannot prevent movement of the corneal flap under the vertical reciprocating motion of the eyelid. A superior or upper hinge, on the other hand, will keep the corneal flap in place under blinking action of the eyelid.

In view of the foregoing it is evident that the present invention is well adapted to attain all of the objects and features hereinabove set forth, together with other objects and features which are inherent in the apparatus disclosed herein.

As will be readily apparent to those skilled in the art, the present invention may easily be produced in other specific forms without departing from its spirit or essential characteristics. The present embodiment is, therefore, to be considered as merely illustrative and not restrictive. The scope of the invention is indicated by the claims that follow rather than the foregoing description, and all changes which come within the meaning and range of equivalence of the claims are therefore intended to be embraced therein.

What is claimed is:

1. A microkeratome cutting blade, comprising:
   a substantially rectangular plate having a sharp edge for cutting;
   said plate having a smooth, continuous bend therein such that the cutting edge is arcuately shaped and does not lie completely within a lateral plane.

2. The cutting blade of claim 1, wherein said plate comprises steel.

3. The cutting blade of claim 1, wherein said plate includes an opening therein for engagement by a blade-holding member of the microkeratome.

4. The cutting blade of claim 1, wherein said plate is elongated across the cutting edge.

5. The cutting blade of claim 1, further comprising a blade holder adapted to engage the plate.

6. The cutting blade of claim 5, wherein the blade holder is adapted to oscillate laterally within a cavity in the microkeratome so as to enhance the performance of the cutting blade.

7. The cutting blade of claim 6, wherein the blade holder includes a slot therein for engagement by a member of the microkeratome to induce oscillatory motion in the cutting blade that is transverse a cutting path defined by the microkeratome.

* * * * *